US 11,992,606 B2

(12) United States Patent
Wiegandt et al.

(10) Patent No.: US 11,992,606 B2
(45) Date of Patent: May 28, 2024

(54) DEVICE AND METHOD FOR DETERMINING AN AEROSOL DELIVERY (71) Applicant: Fraunhofer-Gesellschaft zur Förderung der angewandten Forschung e.V., Munich (DE)

(72) Inventors: Felix Wiegandt, Hannover (DE); Gerhard Pohlmann, Meerbeck (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 716 days.

(21) Appl. No.: 17/256,865

(22) PCT Filed: Jul. 2, 2019

(86) PCT No.: PCT/EP2019/067729
§ 371 (c)(1),
(2) Date: Dec. 29, 2020

(87) PCT Pub. No.: WO2020/007858
PCT Pub. Date: Jan. 9, 2020

(65) Prior Publication Data
US 2021/0252237 A1 Aug. 19, 2021

(30) Foreign Application Priority Data
Jul. 4, 2018 (EP) .................................... 18181682

(51) Int. Cl.
*A61M 15/00* (2006.01)
*A61M 11/04* (2006.01)
(Continued)

(52) U.S. Cl.
CPC ...... *A61M 15/0001* (2014.02); *A61M 11/041* (2013.01); *G01N 15/0606* (2013.01);
(Continued)

(58) Field of Classification Search
CPC .............. A61M 15/00; A61M 15/0085; A61M 2205/3306; A61M 2205/8206;
(Continued)

(56) References Cited

U.S. PATENT DOCUMENTS 8,711,338 B2  4/2014  Liu
2005/0073683 A1  4/2005  Gard
(Continued)

FOREIGN PATENT DOCUMENTS

CN         103889488 A  *  6/2014  ............ A61M 11/00
DE   10 2013 103 152 B3     12/2013
(Continued)

OTHER PUBLICATIONS

International Search Report and Written Opinion dated Jul. 26, 2019 in International Application No. PCT/EP2019/067729.
(Continued)

*Primary Examiner* — Michael P Stafira
(74) *Attorney, Agent, or Firm* — Knobbe, Martens, Olson & Bear, LLP (57) ABSTRACT A device for determining delivery of an aerosol stream has a collector having a filter for collecting aerosol particles in the aerosol stream, a first fluid connection point connectable to an aerosol generator, and a second fluid connection point connectable to a breathing simulator for simulating tidal breathing, at least one measurement volume for an interaction of at least one light beam with the aerosol particles passing through the measurement volume, at least one optical measurement unit for generating at least one optical measurement signal depending on the interaction of the at least one light beam with the aerosol particles passing the measurement volume, determines an absorption and/or adsorption of a liquid on aerosol particles.

16 Claims, 6 Drawing Sheets

(51) Int. Cl.
*G01N 15/06* (2006.01)
*G01N 15/075* (2024.01)

(52) U.S. Cl.
CPC .............. *A61M 2205/3306* (2013.01); *A61M 2205/3379* (2013.01); *A61M 2205/75* (2013.01); *G01N 15/075* (2024.01)

(58) Field of Classification Search
CPC ........ A61M 11/005; A61M 2016/0021; A61M 16/06; A61M 2205/3569; A61M 2205/52; A61M 15/0028; A61M 2205/3592; A61M 2209/02; A61M 11/00; A61M 15/0065; A61M 2205/3379; A61M 2205/0233; A61M 2205/583; A61M 2205/6072; A61M 16/024; A61M 2205/6054; A61M 15/009; A61M 16/14; A61M 2205/3327; A61M 2205/3334; A61M 2205/6045; A61M 15/0031; A61M 15/0033; A61M 15/025; A61M 16/04; A61M 16/08; A61M 2016/0024; A61M 2205/8262; A61M 2209/082; A61M 2205/581; A61M 11/001; A61M 15/0021; A61M 2016/0039; A61M 2205/3584; A61M 2205/505; A61M 15/008; A61M 15/0086; A61M 16/0003; A61M 2205/502; A61M 15/002; A61M 16/0051; A61M 2205/33; A61M 2205/3553; A61M 2205/7536; A61M 2230/40; A61M 15/0081; A61M 15/0083; A61M 15/06; A61M 16/021; A61M 2205/276; A61M 2205/3313; A61M 2205/584; A61M 2205/6018; A61M 11/042; A61M 16/00; A61M 2016/0015; A61M 2205/3331; A61M 2205/70; A61M 11/041; A61M 15/0001; A61M 15/0013; A61M 15/0018; A61M 16/026; A61M 2016/0027; A61M 2205/3317; A61M 2205/3561; A61M 2205/3653; A61M 2205/50; A61M 2205/582; A61M 2205/75; A61M 2207/00; A61M 15/0068; A61M 16/10; A61M 2202/0208; A61M 2205/0227; A61M 2205/0238; A61M 2205/13; A61M 2205/15; A61M 2205/18; A61M 2205/43; A61M 2205/587; A61M 2206/11; A61M 2230/06; A61M 2230/205; A61M 2230/30; A61M 11/002; A61M 11/003; A61M 15/0003; A61M 15/0035; A61M 15/0091; A61M 15/0096; A61M 16/0066; A61M 16/022; A61M 16/107; A61M 16/1075; A61M 16/108; A61M 16/142; A61M 2016/0018; A61M 2016/0036; A61M 2205/0294; A61M 2205/103; A61M 2205/27; A61M 2205/6027; A61M 11/007; A61M 2205/3368; A61M 2205/44; A61M 2205/6009; A61M 2205/6063; A61M 2205/609; A61M 2207/10; A61M 15/001; A61M 15/0026; A61M 15/0051; A61M 15/0063; A61M 15/0071; A61M 15/02; A61M 16/0006; A61M 16/0404; A61M 16/0434; A61M 16/044; A61M 16/0481; A61M 16/0486; A61M 16/0833; A61M 16/201; A61M 2016/003; A61M 2016/0033; A61M 2202/06; A61M 2202/064; A61M 2205/3324; A61M 2205/3386; A61M 2205/3396; A61M 2205/35; A61M 2205/60; A61M 2205/707; A61M 2205/82; A61M 2205/8237; A61M 2210/1039; A61M 2230/43; A61M 2230/50

See application file for complete search history.

(56) References Cited

U.S. PATENT DOCUMENTS

| | | |
|---|---|---|
| 2011/0310386 A1 | 12/2011 | Renard et al. |
| 2014/0247450 A1* | 9/2014 | Han .................. G01N 15/0211 356/338 |
| 2015/0020804 A1* | 1/2015 | Van Der Mark .. G01N 15/0211 128/203.14 |
| 2016/0000358 A1 | 1/2016 | Lundin |
| 2017/0097294 A1 | 4/2017 | Karakaya |

FOREIGN PATENT DOCUMENTS

| | | | |
|---|---|---|---|
| DE | 10 2013 103152 | 12/2013 | |
| DE | 102013103152 B3 * | 12/2013 | ......... G01N 15/0618 |
| EP | 0 539 674 | 5/1993 | |
| EP | 0539674 A1 * | 5/1993 | |
| EP | 3203397 A1 * | 8/2017 | ............ A61M 15/00 |
| JP | 2012-509486 A | 4/2012 | |
| WO | WO 2015/189089 | 12/2015 | |
| WO | WO 2017/133045 A1 | 8/2017 | |
| WO | WO 2018/010954 A1 | 1/2018 | |

OTHER PUBLICATIONS

Office Action dated Nov. 24, 2022 in EP Application No. 19 735 315.4.

* cited by examiner

DEVICE AND METHOD FOR DETERMINING AN AEROSOL DELIVERY

PRIORITY AND CROSS REFERENCE TO RELATED APPLICATIONS

This application is the U.S. National Stage Application under 35 U.S.C. § 371 of International Application No. PCT/EP2019/067729, filed Jul. 2, 2019, designating the U.S. and published in English as WO 2020/007858 on Jan. 9, 2020, which claims the benefit of European Patent Application No. EP 18181682.8, filed Jul. 4, 2018. Any and all applications for which a foreign or a domestic priority is claimed is/are identified in the Application Data Sheet filed herewith and is/are hereby incorporated by reference in their entirety under 37 C.F.R. § 1.57.

FIELD OF THE INVENTION

The present invention relates to a device and a method for determining an aerosol delivery of an aerosol stream, in particular a dry aerosol stream or a humid aerosol stream comprising an absorbed liquid and/or an absorbed liquid, and a method for determining an absorption and/or adsorption of a liquid on aerosol particles.

RELATED ART

Pulmonary or respiratory diseases, including but not limited to asthma or chronic obstructive pulmonary disease (COPD), are usually treated by an inhalation of drugs which are provided as liquid or solid particles in an aerosol stream. Herein, the particles which are generated by using an aerosol generator, preferably, exhibit a size that they become respirable by the alveoli and the lungs. In this regard, devices and methods for determining an aerosol delivery of an aerosol stream, in particular of a dry aerosol stream or of a humid aerosol stream comprising an absorbed liquid and/or an absorbed liquid, provided by the aerosol generator are used for developing relevant test parameters.

DIN EN 13544-1:2007+A1:2009 describes a method and a device for determining an aerosol delivery of an aerosol stream being provided by an aerosol generator. The device comprises a collecting unit which has a filter for collecting aerosol particles being provided by the aerosol stream. The collecting unit has a first fluid connection point which is located, with respect to a direction of the aerosol stream, in front of the filter and is connected to the aerosol generator, and a second fluid connection point which is located, with respect to the direction of the aerosol stream, behind the filter and is connected to a breathing simulator, which is designated for simulating tidal breathing characterized by consecutive inhalation and exhalation.

For determining the aerosol delivery of the aerosol stream, in particular of the dry aerosol stream or a humid aerosol stream, which is provided by the aerosol generator, the aerosol generator is connected to a breathing simulation unit, in particular to a sinusoidal pump, which is designated for simulating the breathing flow. The filter is placed between the aerosol generator and the breathing simulation unit. The aerosol generator is filled with definite amount of an aerosolizable substance, specifically a 1 molar aqueous solution of sodium fluoride (NaF), and is operated until the generation of the aerosol is finished. Hereinafter, a quantitative chemical analysis is performed.

The filter is selected in a manner that it is capable of retaining at least 95% of the aerosols. For this purpose, high-performance filters of polypropylene can, in particular, be used. A dead volume between a distal end of a patient interface and a corresponding surface of the filter should, however, be limited to 10% or less of the respiratory stroke volume or tidal volume, which corresponds to an approximate volume of 0.5 liters for an adult person or less than 5 ml for preterm neonates. In order to meet this requirement, a flat filter is, usually, employed.

However, flat filters, typically, have a low capacity. This feature severely limits the applicability of flat filters with respect to large aerosol amounts since frequent filter replacements may lead to a considerably high number of individual filters which require a quantitative chemical analysis. As a result, a delivery of measurement results is delayed. In addition, a use of humidified aerosols further requires a sophisticated conditioning of the filters in case of a gravimetric determination of an aerosol sample, which results in an additional delay of the delivery of the measurement results.

DE 10 2013 103 152 B3 discloses a method and a device for determining an aerosol delivery of an aerosol stream being provided by an aerosol generator. The device comprises a collecting unit which has a filter for collecting aerosol particles being provided by the aerosol stream. In addition to a first fluid connection point which is connected to the aerosol generator and a second fluid connection point which is connected to a breathing simulator as already described in DIN EN 13544-1:2007+A1:2009, the collecting unit has at least one third fluid connection point which is connected with a gas flow unit for generating a gas stream. The third fluid connection point is arranged in a manner that the aerosol stream is at least partially directed by the gas stream to the filter.

Herein, a closed ventilatory circuit is established between the aerosol generator and the sinusoidal pump. Thus, the aerosol stream is directed from a distal end of a patient interface to the corresponding surface of the filter in a loop. Consequently, the aerosol particles leave a proximal end of the patient interface only in an event in which the sinusoidal pump exerts an inhalation stroke. In this event, the particles are extracted from the patient interface and deposited on the filter. As a result, only the volume between the distal end and the proximal end of the patient interface can be considered as the dead volume. Thus, this method and device for determining the aerosol delivery is also applicable for small tidal volumes which, in particular, are typical for infants, babies, neonates, and preterm neonates.

WO 2017/133045 A1 discloses an aerosol real-time monitor comprising a laser light source assembly for emitting a laser beam and forming a line-shaped laser spot at a particle excitation position of air flow to be tested; an enclosed photoelectric measurement room, wherein the laser light source assembly is provided at a laser entrance port at the rear end of the enclosed photoelectric measurement room; inside the enclosed photoelectric measurement room, the air flow to be tested and the optical axis of the laser beam, emitted by the laser light source assembly, in a traveling direction intersect at the particle excitation position where the line-shaped laser spot is; a scattered light signal reflecting mirror and a fluorescence signal reflecting mirror bilaterally and symmetrically provided to center a measurement point formed by intersection of the laser beam emitted by the laser light source assembly and the air flow to be tested; a scattered light signal detector and a fluorescence signal detector used to detect a scattered light signal and a fluorescence signal passing through openings of the reflecting mirrors. The portable monitor is capable of online monitoring.

US 2005/073683 A1 discloses a method and an apparatus for identifying individual aerosol particles in real time. Sample aerosol particles are collimated, tracked, and screened to determine which ones qualify for mass spectrometric analysis based on predetermined qualification or selection criteria. Screening techniques include one or more of determining particle size, shape, symmetry, and fluorescence. Only qualifying particles passing all screening criteria are subject to desorption and/or ionization and single particle mass spectrometry to produce corresponding test spectra, which are used to determine the identities of each of the qualifying aerosol particles by comparing the test spectra against predetermined spectra for known particle types. However, an application of this method and apparatus results in a modification of the particles through ionization of the particles.

U.S. Pat. No. 8,711,338 B2 discloses a method and an apparatus for detecting particles in a gas by saturating the gas with vapor and causing the gas to flow through a chamber with walls that are at a temperature different than the temperature of the entering gas, thereby creating a gas turbulence within the chamber in a manner that the gas is becoming super-saturated with vapor and causing the super-saturated vapor to condense on the particles and form droplets, which are then detected and counted by an optical light-scattering detector. However, this method and apparatus is not capable for detecting particles in real time. WO 2018/010954 A1 discloses a device for a respiration-controlled application of aerosol in powder form during the artificial respiration or assisted respiration of a patient, the system comprising the following elements: an interface) which can be brought into contact with the respiratory tract of the patient to be artificially respirated or supported in respiration, a unit for generating a respiratory gas flow, wherein the respiratory gas flow has a first pressure which is higher than or equal to the ambient pressure, at least one inspiration line through which the respiratory gas flow is conducted to the interface, an aerosol generator, at least one aerosol line through which the generated aerosol in powder form is conducted from the aerosol generator to the interface, and a respiration sensor.

EP 0 539 674 A1 discloses an aerosol generator useful as an atomizer for controllably and reproducibly producing wet or dry aerosols for inhalation studies, including a nebulizer for producing an aerosol from a liquid and an air stream, a liquid dosing device such as a step dosing pump for controllably feeding a liquid to be atomized to the nebulizer, an apparatus such as a mass flow controller for regulating the flow of an air stream to the nebulizer to provide an amount needed to atomize the liquid, and optionally to dilute the resulting aerosol, a conduit for conveying the aerosol formed in the nebulizer to an aerosol exposure chamber, a measuring device such as a light-scattering diffusion photometer into which a sample of the aerosol is introduced for determining the concentration of the aerosol, and a control unit for controlling the liquid supply device and the adjustable air supply to produce an aerosol having a predetermined desired concentration; the control unit being operated either manually or by a computer responsive to measured values determined by the measuring device.

WO 2015/189089 A1 discloses a sensor system for measuring particle concentration and mass concentration in an aerosol. An optical sensor is used for measuring a particle concentration and a mechanical sensor is used for measuring a mass of collected particles. A particle concentration in the aerosol is monitored using the optical sensor, until detection of a particle generating event. Upon detection of a particle generating event, a mass measurement using the mechanical sensor is performed and the mass measurement is used to calibrate the optical sensor.

US 2016/000358 A1 discloses a diagnostic device for characterization of particles from a patient's airways, such as a lung, when ventilated by a ventilator, and/or for control thereof, comprising a particle detecting unit configured to be connected to a conduit for passing expiration fluid from said patient, for obtaining data related to particles being exhaled from said patient's airways.

In addition, known methods and devices for determining an absorption of a liquid, in particular water or an aqueous solution, by the particles or an adsorption of the liquid on a surface of the particles require a chemical analysis of a sample comprising the particles whereby the particles are modified and, eventually, destroyed.

It is therefore an objective of the present invention to provide a device and a method for determining an aerosol delivery of an aerosol stream which at least partially avoids the above-mentioned problems.

In particular, it would be desirable to be able to use a device and a method which would allow determining the aerosol delivery of the aerosol stream which comprises liquid or solid particles in a simple and quantitative manner in real time and for both large and low tidal volumes in order to be applicable to adult persons but also to infants, babies, neonates, and preterm neonates. Hereby, it would be desirable if the determination could also be used in an event of triggered release of particles that may, in particular, be synchronized with the breathing.

In addition, it would be desirable to, alternatively or in addition, use the device in a method for determining an absorption and/or adsorption of a liquid, in particular water or an aqueous solution, on aerosol particles which could be performed in real time.

SUMMARY OF THE INVENTION

This problem is solved by a device and a method for determining an aerosol delivery of an aerosol stream as well as by a method for determining an absorption and/or adsorption of a liquid on aerosol particles having the features of the independent claims. Preferred embodiments, which might be implemented in isolated fashion or in any arbitrary combination, are subject matter of the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect, the present invention refers to a device for determining an aerosol delivery of an aerosol stream generated by an aerosol generator.

As generally used, the term "aerosol" refers to an aerosolizable material that comprises solid or liquid particles of a substance which are suspended in a gas phase, wherein the particles may, in particular, be or comprise particles of a pharmaceutical preparation, such as, for example, a lung surfactant. For converting the particles into this state, an aerosolizable material, i.e. powder or a liquid solution, is treated in an "aerosol generator", also denoted as "aerosolization device", by vibrating meshes or ultrasonic waves in order to entrain the solid or liquid particles into a gas stream of a carrier gas, such as a respiratory gas. In this state, the particles are, preferably, distributed across the entire volume of the carrier gas, in particular, in a uniform and finely dispersed form. As a result, the aerosol is provided as an "aerosol stream" in which the solid or liquid aerosol particles are borne and/or carried by the carrier gas stream. In particular, the aerosol stream may comprise a dry aerosol stream or a humid aerosol stream, wherein the terms "humid aerosol" or "humidified aerosol" refer to aerosol particles in which the aerosol particles have a liquid absorbed and/or adsorbed on at least one of their surfaces. For this purpose, the solid particles may, in addition, be treated in a so-called "humidifier" to generate a humidified aerosol which comprises a relative amount of vapor in addition to the carrier gas.

As further used herein, the term "aerosol delivery" refers to providing the aerosol to a predefined volume, in particular to a patient interface or to a measurement volume. Herein, the "measurement volume" defines a volume in which a measurable quantity of the aerosol is determined which is, preferably, placed in a location being passed by the aerosol stream on its path between the aerosol generator and the patient interface or, alternatively or in addition, in a diversion leading off this path. As generally used, the term "patient" relates to a human being of any age, in particular, including children, babies, neonates and preterm neonates. Further, the term "ventilation" relates to a process of accomplishing a movement of the respiratory gases in the airways of the patient, in particular, via alternating steps of inhalation and exhalation. In contrast to normally breathing patients who are capable of performing the circulation without any additional aids, patients who are subject to respiratory support during spontaneous breathing or mechanical ventilation, require the respiratory gases at least partially to be provided from the ventilator via a ventilatory circuit. As generally used, "mechanical ventilation" refers to a partial or full adoption of HI physiological breathing by external aids, specifically at insufficient spontaneous breathing or a complete breakdown thereof. Further, "respiratory support" refers to a support during spontaneous breathing by applying a continuous positive airway pressure (CPAP) over the whole breathing cycle, in particular, in order to avoid a collapse of the alveoli and smaller breathing conducts during exhalation. Hereby, the patient can adjust parameters, including but not limited to depth of respiration, respiratory rate, or air flow, which, in general, requires that the patient is still capable of his own breathing.

Further, the term "ventilatory circuit" refers to a device being configured for respiratory support or mechanical ventilation of respiratory gases as provided by a ventilator to a patient and from the patient back to the ventilator, hereby excluding the respiratory tracks of the patient. Further, the term "patient interface" relates to a unit being configured for providing a connection between the ventilatory circuit and the respiratory track of the patient which is therefore, in general, located adjacent to the patient. For this purpose, the patient interface may be integrated into, or attached to, the ventilatory circuit, wherein the ventilatory circuit may, in general, comprise a ventilator and tubes adapted for guiding gases from the ventilator to a patient interface and back. In particular, a suitable mouthpiece, a breathing mask, a nasal cannula or a tracheal cannula may be part of the patient interface or attachable thereto. However, other arrangements of the patient interface may also be feasible.

According to the present invention, an aerosol delivery is determined in the measurement volume, wherein the "aerosol delivery" is a physical quantity referring to any one of a number, a volume, or a mass of aerosol particles passing through the measurement volume. Alternatively or in addition, an aerosol delivery rate may also be determined by employing the present invention when the term "aerosol delivery" is used. As generally used, the "aerosol delivery rate" is a physical quantity referring to any one of a number, a volume, or a mass of aerosol particles passing through the measurement volume within a predefined time interval. By way of example, the aerosol delivery may refer to a number, a volume, or a mass of aerosol particles which are delivered to the patient interface. Similarly, the aerosol delivery rate may refer to a number, a volume or a mass of aerosol particles which are delivered to the patient interface within a time interval, such as a second, a minute or an hour. However, further kinds of units may also be feasible.

Further according to the present invention, an absorption and/or adsorption of a liquid on the aerosol particles may, alternatively or in addition, be determined, wherein the "absorption and/or adsorption of a liquid on the aerosol particles" is a physical quantity which relates to any one of a number, surface area, a volume, or a mass of a liquid, in particular of water or an aqueous solution which is absorbed by the aerosol particles and/or adsorbed on a surface of the aerosol particles. By way of example, the absorption and/or adsorption of water may refer to a relative volume or mass of water as comprised by the humidified aerosol particles. However, further kinds of units may also be feasible.

Accordingly, the device according to the present invention comprises:
- a collecting unit, the collecting unit having a filter designated for collecting aerosol particles carried by an aerosol stream, a first fluid connection point which is connectable to an aerosol generator, and a second fluid connection point which is connectable to a breathing simulator being designated for simulating tidal breathing;
- at least one measurement volume which is designed for an interaction of at least one light beam with the aerosol particles carried by the aerosol stream and passing through the measurement volume;
- at least one optical measurement unit which is designed for generating at least one optical measurement signal depending on the interaction of the at least one light beam with the aerosol particles passing the measurement volume; and at least one evaluation unit which is designed for determining the aerosol delivery of the aerosol stream from the at least one optical measurement signal.

Thus, the device according to the present invention comprises a collecting unit, at least one measurement volume, at least one optical measurement unit, and at least one evaluation unit. Herein, the components listed above may be separate components. Alternatively, two or more of the components as listed above may be integrated into one component. Further, the at least one evaluation unit may be formed as a separate evaluation unit independent from the optical measurement unit but may, preferably, be connected to the optical measurement unit in order to receive the corresponding optical measurement signal. Alternatively, the at least one evaluation unit may fully or partially be integrated into the optical measurement unit.

As indicated above, the collecting unit has a filter which is designated for collecting aerosol particles carried by the aerosol stream, a first fluid connection point which is connectable to an aerosol generator, and a second fluid connection point which is connectable to a breathing simulator being designated for simulating tidal breathing. As generally used, the collecting unit is a device which is designed for supplying an aerosol stream to a filter which is used for collecting aerosol particles carried by the aerosol stream and, subsequently, to guide away the aerosol stream from the filter. As generally used, the term "filter" refers to a device which is capable of collecting particles which are supplied by a gas steam to a surface of the filter by deposition of at least some of the particles on the surface of the filter which is faces a direction of the gas stream. Herein, the gas stream is supplied by an aerosol generator to which the collecting unit is connectable by using the first fluid connection point. Further, by using the second fluid connection point the collecting unit is connectable to a breathing simulator which supports the collecting unit in guiding away the aerosol stream after having passed the filter. As generally used, the "breathing simulator" relates to a device which is, specifically, designated for simulating tidal breathing by consecutive inhalation and exhalation, such as described in DIN EN 13544 cited above. As a result, the aerosol particles are deposited on the filter in a manner comparative to the particles which are inhaled by a patient, thus, allowing a realistic estimation of the aerosol delivery of the aerosol stream being available for inhalation by the patient.

According to the present invention, the device comprises a collecting which unit may be embodied in a fashion as described in DIN EN 13544 cited above. Thus, the first fluid connection point may be located, with respect to a direction of the aerosol stream, in front of the filter, wherein the second fluid connection point may be located, again with respect to the direction of the aerosol stream, behind the filter and is connected to the breathing simulator. For further details, reference may be made to DIN EN 13544. As generally used, the "fluid connection point" relates to a location in a particular fluid line carrying a gas or aerosol stream where an additional gas stream may be introduced into the particular fluid line or guided away from the particular fluid line. In an alternatively preferred embodiment, the collecting unit may be based on DE 102013103152 B3, thus, having at least one third fluid connection point which can be connected with a gas flow unit for generating a gas stream, wherein the third fluid connection point may be arranged in a manner that the aerosol stream may at least partially directed by the gas stream to the filter. For further details, reference may be made to the disclosure of DE 102013103152 B3. However, further embodiments for the collecting unit may be conceivable.

Further according to the present invention, the device comprises at least one measurement volume. As generally used, the "measurement volume" refers to an extended volume in space which is designated for performing a desired measurement. Herein, the measurement volume is specifically designed for allowing an interaction of the aerosol particles with at least one light beam (or vice versa), in particular by using an adapted guiding of both the light beam and of the particles within the measurement volume. In order to be able to measure all aerosol particles as carried by the aerosol stream, the measurement volume may, preferably, be located between the first fluid connection point and the filter, i.e. upstream with respect to the filter which is, as already described above, designed for collecting the aerosol particles.

Thus, the measurement volume is designed for allowing the aerosol stream passing through the measurement volume. In particular, the measurement volume may, preferably, comprise walls having an internal surface which may be smooth and free of edges, recesses and protrusions as far as possible. As a result, the aerosol stream may, thus, be capable of passing the measurement volume with as little influence by form and arrangement of the measurement volume as possible. This effect may ensure that as few aerosol particles as possible may be deposited on the walls of the measurement volume prior to be deposited on the filter as described above in more detail. In this manner, an undesired staining of the enclosing surfaces of the measurement volume, especially of the optical windows, which may result in an undesired signal loss of the light beam can, thus, be avoided.

As used herein, the term "interaction" refers to an encounter of the aerosol particles with the light beam, by which action the light beam may be altered in a fashion that it experiences an alteration that may be in a relationship with at least one physical property of the aerosol particles having an encounter with the light beam when passing through the measurement volume. As a result, the alteration of the light beam following this encounter with the aerosol particles passing through the measurement volume is capable of allowing a determination of the physical property of the of the aerosol particles provided that the relationship between the alteration of the light beam and the physical property of the aerosol particles is known. A particularly preferred manner of determining this relationship is described below in more detail.

Further according to the present invention, the device comprises at least one optical measurement unit which is designed for generating at least one optical measurement signal that depends on the interaction of the at least one light beam with the aerosol particles passing the measurement volume. As used herein, the "optical measurement unit" refers to a device having at least one optical sensor which is designated for generating the at least one optical measurement signal by surveilling the alteration of the light beam, thus, as described above, allowing the determination of the physical property of the of the aerosol particles. As generally used, the terms "optical" and "light" refer to electromagnetic radiation in the visible spectral range which may also include the adjacent infrared spectral range and ultraviolet spectral range. Referring to ISO standard ISO-21348, if in doubt, in a version applicable at the date of application of this document, the "visible spectral range" generally relates to a wavelength of 380 nm to 760 nm, whereas the "infrared spectral range" generally refers to a wavelength of 760 nm to 1000 µm, wherein the wavelength of 760 nm to 1.4 µm is usually denoted as "near infrared spectral range", and whereas the "ultraviolet spectral range" refers to a wavelength of 1 nm to 380 nm, preferably of 100 nm to 380 nm. Preferably, light used within the present invention is visible light, i.e. light in the visible spectral range having a wavelength of 380 nm to 760 nm.

In a particularly preferred embodiment, the alteration of the light beam that is surveilled by the optical measurement may be an extinction of the light beam in the measurement volume upon the passing of the aerosol particles. As generally used, the "extinction of the light beam" relates to an attenuation of the light beam following the encounter of the light beam with one or more of the aerosol particles taking place within the measurement volume. Thus, a grade of the extinction of the light beam results in an optical measurement signal that may be used for determining the desired physical property of the aerosol particles as described below in more detail. Alternatively or in addition, other kinds of alterations of the light beam may be measured by the optical measurement unit, such an alteration of a transmission, an absorption, a diffraction, a reflection, a refraction, a scattering, or a polarization of the light beam.

The light beam which is used for interaction with the aerosol particles carried by the aerosol stream within the measurement volume may be provided by at least one illumination source which is designated to emit at least one light beam for this purpose. Herein, the illumination source can comprise at least one of the following illumination sources: a laser, in particular a laser diode, although in principle, alternatively or additionally, other types of lasers can also be used; a light emitting diode; an organic light source, in particular an organic light emitting diode; a structured light source. Alternatively or additionally, other illumination sources may also be feasible.

In a particularly preferred embodiment, the optical measurement unit may further be designated for providing the at least one light beam. For this purpose, the optical measurement unit may be or comprise a laser measurement system, wherein the laser measurement unit may also designed for providing the at least one light beam in addition to having the at least one optical sensor being designated for generating the at least one optical measurement signal by surveilling the alteration of the light beam. Herein, the laser measurement unit is capable of generating at least one laser beam which may, specifically, be provided in form of a single narrow beam which may pass the measurement volume in a static or a dynamic fashion. Preferably, the light beam, in particular the laser beam, may exhibit a small aperture in all directions apart from a direction being perpendicular to the direction of the aerosol stream, thus, allowing a surveillance of at least a part of, preferably of all of, the aerosol particles that pass the measurement volume within a time interval being required for the aerosol particles to pass the aperture of the light beam in the direction of the aerosol stream. As used herein, the term “perpendicular” refers to a value of 90° but may also include a deviation of ±15°, preferably of ±5°, more preferred of ±1°, specifically of ±0.1°, from the perpendicular arrangement. In a particular embodiment, the light beam may, thus, be adapted to illuminate a light sheet within the measurement volume, specifically, a sheet that may be perpendicular to the direction of the aerosol stream. As generally used, the term “sheet” refers to a two-dimensional extension of the light in contrast to a one-dimensional extension of the light in a beam.

In a particularly preferred embodiment, the measurement volume may be separated from the optical measurement unit by at least one optical window. As generally used, the term “optical window” refers to a device which is designated for being passed by the at least one light beam when entering or leaving the measurement volume. As a result, the optical windows, thus, allows guiding the aerosol stream through the measurement volume with as little deviation as possible by entering or leaving of the light beam into the measurement volume. Further, in order to influence the light beam as little as possible, the optical window may comprise an optically at least partially transparent material, preferably a material which may exhibit a high optical transparency at the at least one wavelength of the light beam. For this purpose, the optically at least partially transparent material may, in addition, be substantially homogeneous and free of embedded particles, specifically in order to avoid an undesired signal loss, for example following a scattering of the light beam at embedded particles. Herein, the optical window and the respective wall of the measurement volume may be provided from the same material or from different materials. Thus, the optical window may be comprised by the wall or may be provided as a separate unit being attached to the wall, e.g. by using an adhesive, from inside or from outside with respect to the measurement volume.

In a further particularly preferred embodiment, the optical window may be arranged in a fashion that the light beam can pass the optical window in a perpendicular manner. As also used here, the term “perpendicular” refers to a value of 90° but may also include a deviation of ±15°, preferably of ±5°, more preferred of ±1°, specifically of ±0.1°, from the perpendicular arrangement. As a result of this arrangement, a further undesired signal loss following an undesired refraction of the light beam entering or leaving the optical window, which may, in general, exhibit a refractive index that is different from the refractive index of the at least one substance comprised by the measurement volume, may, thus, at least partially be avoided.

In a further particularly preferred embodiment, the optical window may exhibit a thickness which may be as low a possible, thereby keeping a mechanical stability of the optical window within a desired range. Thus, a further undesired signal loss following an attenuation of the light beam passing the optical window may partially be avoided.

In a particularly preferred embodiment, the laser beam may be emitted from a laser emitter and pass through a first optical window towards the measuring volume in which the aerosol particles are, preferably, present. By a presence of the aerosol particles, the laser beam may be attenuated, may pass through the second optical window which is located on the opposite side and may be captured by a laser receiver.

In an alternative embodiment, the light beam may impinge an opposite side of the measurement volume where it may be reflected in order to be guided to the optical measurement unit. Herein, the light beam may be reflected in a fashion that it may or, preferably, may not pass the measurement volume at least partially again. Thus, in a particular embodiment, the light beam may be reflected in a manner that it may take the same path back through the measurement volume and, if applicable, through the optical window to the optical measurement unit. This kind of arrangement may allow increasing the optical measurement signal by a factor of approximately 2, thus, increasing a sensitivity of the optical measurement signal.

Thus, in a particularly preferred embodiment, the measurement volume may be separated from the optical measurement unit by two opposing optical windows, wherein the two opposing optical windows may be arranged with respect to each other in a parallel manner. As used herein, the term "parallel" refers to a value of 180° but may also include a deviation of ±15°, preferably of ±5°, more preferred of ±1°, specifically of ±0.1°, from the parallel arrangement. Further, it may be advantageous to arrange the two opposing optical windows as close as reasonable with respect to each other. Although a close arrangement of the two opposing optical windows may be capable of decreasing the sensitivity of the optical measurement signal, it may, concurrently, increase unwanted multiple scattering within the measurement volume. In order to reduce signal losses, it may further be advantageous to arrange the illumination source and/or the optical sensor as close as possible to the corresponding optical window.

In a further particular embodiment, the device may, additionally, comprise a heating unit that may be designated for heating the at least one optical window. As a result thereof, the at least one optical window can be kept free from any moisture and particle deposition, specifically, thus avoiding an undesired signal loss of a light beam passing an optical window being stained by particle and moisture deposition. Specifically, the heating unit can be provided in form of a heating cabinet that may be capable of receiving the device or at least a part thereof comprising the measurement volume and the at least one optical window separating the measurement volume from the optical measurement unit.

In a further particular embodiment, the device may comprise two individual measurement volumes. Herein, at least one first optical measurement unit can be designed for generating at least one first optical measurement signal depending on the interaction of at least one first light beam with the aerosol particles passing the first measurement volume in the inhalation phase of the breathing simulator, and the evaluation unit can be designed for determining the first aerosol delivery of the aerosol stream during the inhalation phase from the first optical measurement signal. Similarly, at least one second optical measurement unit can be, further, designed for generating at least one second optical measurement signal depending on the interaction of at least one second light beam with the aerosol particles passing the second measurement volume in the exhalation phase and the evaluation unit can be designed for determining the second aerosol delivery of the aerosol stream during the exhalation phase from the second optical measurement signal. Thus, in this particular embodiment, the first aerosol delivery of the aerosol stream during the inhalation phase and the second aerosol delivery of the aerosol stream during the exhalation phase can, separately, be determined.

Further according to the present invention, the device comprises at least one evaluation unit which is designed for determining desired items of information, i.e. the aerosol delivery of the aerosol stream and, optionally, the absorption and/or adsorption of a liquid on aerosol particles, from the at least one optical measurement signal. Preferably, one optical measurement signal may be sufficient for a dry aerosol stream whereas at least two optical measurement signals may be preferable for a humid aerosol stream, specifically in order to determine an offset caused by a liquid absorption and/or adsorption. As used herein, the term "evaluation unit" refers to a device designed to generate the desired items of information, i.e. the aerosol delivery of the aerosol stream from the at least one optical measurement signal. For this purpose, the evaluation unit may be or may comprise one or more integrated circuits, such as one or more application-specific integrated circuits (ASICs), and/or one or more data processing devices, such as one or more computers, preferably one or more microcomputers and/or microcontrollers. Additional components may be comprised, such as one or more preprocessing devices and/or data acquisition devices, such as one or more devices for receiving and/or preprocessing of the sensor signals, such as one or more AD-converters and/or one or more filters. As used herein, the optical measurement signal may generally refer to one of the sensor signals. Further, the evaluation unit may comprise one or more data storage devices. Further, as outlined above, the evaluation unit may comprise one or more interfaces, such as one or more wireless interfaces and/or one or more wire-bound interfaces. The device has, as described above, at least one evaluation unit. In particular, the at least one evaluation unit can further be designed to completely or partly control or drive the device, specifically, by the evaluation unit being designed to control the at least one optical measurement unit.

The evaluation unit can be designed to carry out at least one measurement cycle in which one or a plurality of optical measurement signals are recorded for further evaluation in the evaluation unit. Fort his purpose, the at least one evaluation unit may be adapted to perform at least one computer program, in particular by implementing any one or all of the methods steps as described herein. As an example, one or more algorithms may be implemented which, by using the optical measurement signals as input variables, may determine the desired items of information.

For further details with respect to the device, reference may be made to the description of the device, the exemplary embodiments thereof and the methods as described herein.

In a further aspect, the present invention refers to a method for determining an aerosol delivery of an aerosol stream. As used herein, this method comprises the following steps a) to d):

a) providing an aerosol stream generated by an aerosol generator;
b) guiding aerosol particles carried by the aerosol stream through at least one measurement volume and providing an interaction of the aerosol particles with at least one light beam within the measurement volume;
c) generating at least one optical measurement signal depending on the interaction of the at least one light beam with the aerosol particles passing the measurement volume; and
d) determining the aerosol delivery of the aerosol stream from the at least one optical measurement signal, wherein a conversion function between the optical measurement signal and the aerosol delivery is used.

Herein, although the indicated steps may be performed in the given order, wherein, preferably, all of the indicated steps may be preformed at least partially concurrently. Further method steps, whether described in this document, such as step e), or not, may, additionally, be performed.

According to step a), an aerosol stream is provided, wherein the aerosol stream is generated by an aerosol generator. Herein, the aerosol stream may be a dry aerosol stream or a humid aerosol stream comprising an absorbed liquid and/or an absorbed liquid, the delivery and/or delivery rate of which is to be determined by the present method.

According to step b), the aerosol particles carried by the aerosol stream are guided through at least one measurement volume in a manner that an interaction of the aerosol particles with at least one light beam within the measurement volume occurs.

According to step c), at least one optical measurement signal is generated in a manner that the optical measurement signal, preferably the plurality of the optical measurement signals, depends on the interaction of the at least one light beam with the aerosol particles that pass the measurement volume.

According to step d) the aerosol delivery of the aerosol stream is determined from the at least one optical measurement signal, wherein, for a determination thereof, a conversion function between the optical measurement signal and the aerosol delivery is used. For this purpose, the conversion function, such as a conversion factor, can be taken from a table, such as a table stored in a storage device comprised by the evaluation unit. Preferably, the conversion function can be determined, preferably prior to step d) but also concurrently with or after step d), by performing the following step e) at least one single time, preferably a single time:

e) collecting the aerosol particles carried by the aerosol stream in a filter, measuring a particle load on the filer; and determining a conversion function from a relationship between the particle load and the optical measurement signal.

According to step e), the filter as comprised by the collecting device undergoes a gravimetric determination of the load of the aerosol particles. For this purpose, the filter is 35 weighed and afterwards, when inserted into the system, aerosol sampling is started at a first point of time and at a second point of time after loading it with the aerosol particles. As a result, a difference between a second weight as measured at the second point of time and a first weight as measured at the first point of time allows determining the gravimetric load of the aerosol particles received by the filter between the first point of time and the second point of time. Concurrently, from the at least one optical measurement signal, in particular from the plurality of the optical measurement signals, which are recorded for the time interval between the first point of time and the second point of time, an optical signal of the aerosol particles is determined. By generating a relationship between the optical signal and the gravimetric load of the same aerosol particles within the same aerosol stream, the conversion factor can be determined. This procedure according to step e) can, if desired, be repeated several times, preferably for different particle loads, such as to determine the conversion factor with a desired accuracy, such as by using a regression algorithm, specifically a linear regression.

Subsequently, further considering a known value for the aerosol stream, the conversion function can be used in step d) without further performing a gravimetric determination of the load of the aerosol particles according to step e). As a result, preferably, only a single gravimetric determination of the load of the aerosol particles is sufficient for determining an aerosol delivery of an aerosol stream. It is, however, still possible to determine the load of aerosol particles in a gravimetric fashion at any later point of time, if desired.

In a further aspect, the present invention refers to a method for determining an absorption and/or adsorption of a liquid, in particular water or an aqueous solution, on aerosol particles. This method comprises the step e) as previously described and the following step f):

f) generating at least two optical measurement signals for at least two different particle loads of the aerosol particles, measuring the at least two different particle loads of the aerosol particles on at least two different filters, and determining the absorption and/or adsorption of the liquid on the aerosol particles from an assumed zero optical measurement signal.

According to step f), the optical measurement signal is measured for at least two different loads of the aerosol particles on at least two different filters, wherein each of the loads of the aerosol particles on the at least two different filters is determined, preferably in a gravimetric fashion as described with respect to step e). From the optical measurement signal as measured for each of the at least two different loads, an optical measurement signal for a zero particle load on the filter can be extrapolated by employing a suitable algorithm, such as a linear regression. This non-negligible extrapolated optical measurement signal for a zero particle load on the filter is a result of the observation that the optical measurement signal which is obtained by the optical measurement according to the method used herein still comprises an additional contribution due to a liquid, in particular water or an aqueous solution, which is absorbed and/or adsorbed on the aerosol particles, whereas the gravimetric determination of a dried filter only determines the load of the dry aerosol particles on the filter after any liquid components have been removed. In particular, an intercept of the negative x-axis for an assumed zero optical measurement signal corresponds to a mass of the liquid, e.g. in mg, which is absorbed and/or adsorbed on the aerosol particles.

For further details with respect to the methods, reference may be made to the description of the device and of the exemplary embodiments thereof elsewhere in this document.

Consequently, the device and the methods according to the present invention may, thus, particularly allow determining the aerosol delivery of an aerosol stream and, optionally, the absorption and/or adsorption of a liquid on aerosol particles, each in a simple and quantitative manner and in real-time, since it is sufficient to perform a single gravimetric determination of the load of the aerosol particles prior to the subsequent optical measurements which can be performed in real-time. This method and device for determining the aerosol delivery is also applicable for small tidal volumes which, in particular, are typical for infants, babies, and neonates.

BRIEF DESCRIPTION OF THE DRAWINGS

Further optional features and embodiments of the invention will be disclosed in more detail in the subsequent description of preferred embodiments, preferably in conjunction with the dependent claims. Therein, the respective optional features may be implemented in an isolated fashion as well as in any arbitrary feasible combination, as the skilled person will realize. It is emphasized that the scope of the invention may not be restricted by the preferred embodiments. The embodiments are schematically depicted in the Figures. Therein, identical reference numbers in these Figures refer to identical or functionally comparable elements.

In the Figures.

DETAILED DESCRIPTION

Figure 1:
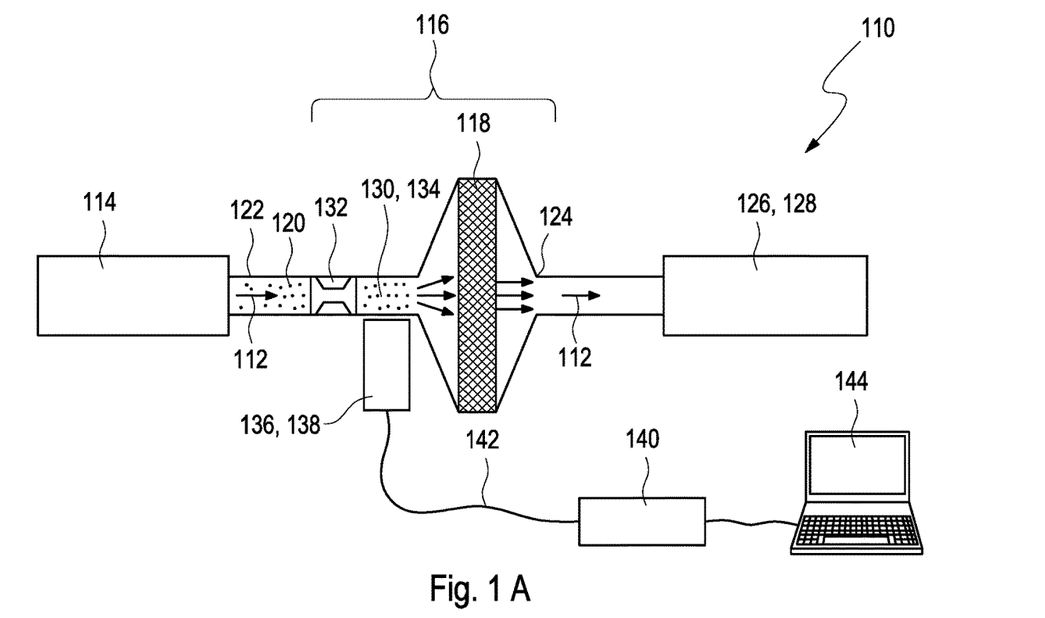
FIGS. 1A to 1C schematically illustrate three preferred embodiments of the device for 35 determining an aerosol delivery of an aerosol stream generated by an aerosol generator.

FIGS. 1A and 1B schematically illustrate two preferred embodiments of the device 110 for determining an aerosol delivery of an aerosol stream 112, in particular of a dry aerosol stream 112 or of a humid aerosol stream 112 comprising an absorbed liquid and/or an absorbed liquid, which may be generated by an aerosol generator 114. As shown in FIGS. 1A and 1B, the device 110 comprises a collecting unit 116, wherein the collecting unit 16 has a filter 118 designated for collecting aerosol particles 120 carried by the aerosol stream 112, a first fluid connection point 122 which is connectable to the aerosol generator 114, and a second fluid connection point 124 which is connectable to a breathing simulator 126, such as a sinusoidal pump 128, which is designated for simulating tidal breathing.

Further, the device 110 comprises a measurement volume 130 which may, preferably, be located downstream with respect to the aerosol stream 112 of an area 132 in which a patient interface may be placed. Herein, the measurement volume 130 is designed for an interaction of at least one light beam (not depicted here) with the aerosol particles 120 carried by the aerosol stream 112 and passing through the measurement volume 130. Herein, the measurement volume 130 may be defined by walls of a conduct 134 that may already be provided for guiding the aerosol stream 112 from the aerosol generator 114 to the filter 118. In the embodiment as depicted here, the first fluid connection point 122 is located, with respect to a direction of the aerosol stream 112, in front of the filter 118 whereas the measurement volume 130 is located between the first fluid connection point 122 and the filter 118.

Further, the device 110 comprises an optical measurement unit 136, preferably being or comprising a laser measurement system 138, which is designed for generating at least one optical measurement signal depending on the interaction of the at least one light beam with the aerosol particles 120 passing the measurement volume 130. In particular, the optical measurement unit 136 is designed for generating the optical measurement signal depending on an extinction of the light beam in the measurement volume 130 upon the passing of the aerosol particles 120 through the measurement volume 130. However, other ways of generating the optical measurement signal, such as a diffraction, a reflection, a refraction, a scattering, or a polarization of the light beam, may also be feasible.

Further, the device 110 comprises an evaluation unit 140 which is designed for determining the desired aerosol delivery of the aerosol stream 112 from the at least one optical measurement signal. Herein, the evaluation unit 140 may be designed for determining the number, volume, or mass of the aerosol particles 120 passing through the measurement volume 130. Alternatively or in addition, an aerosol delivery rate may also be determined, which refers to the aerosol delivery of the aerosol stream 112 passing through the measurement volume 130 within a predefined time interval, such a second, a minute or an hour.

As schematically depicted here, the evaluation unit 140 may be formed as a separate evaluation unit 140 independent from the optical measurement unit 136 but may, preferably, be connected to the optical measurement unit, such as by wire-bound or wireless leads 142 in order to receive the corresponding optical measurement signal. Alternatively (not depicted here), the evaluation unit 140 may fully or partially be integrated into the optical measurement unit 136. As further illustrated here, a monitor 144 which is capable of online monitoring may be used for presenting the determined aerosol delivery of the aerosol stream 112. However, other kinds of output devices may also be feasible.

FIG. 1B illustrates a further preferred embodiment of the device 110 in which the collecting unit 116, in addition to the embodiment as shown in FIG. 1A, further has two third fluid connection points 146 which are connected with a gas flow unit for generating a gas stream 148, wherein the third fluid connection points 146 are arranged in a manner that the aerosol stream 112 is at least partially directed by the gas stream 148 to the filter 118. In the particular embodiment as depicted in FIG. 1B, a centrifugal pump 150 is used for generating a closed circuit 152 of gas within the collecting unit 116. However, other implementations of a closed circuit of gas may also be feasible.

Figure 1C:
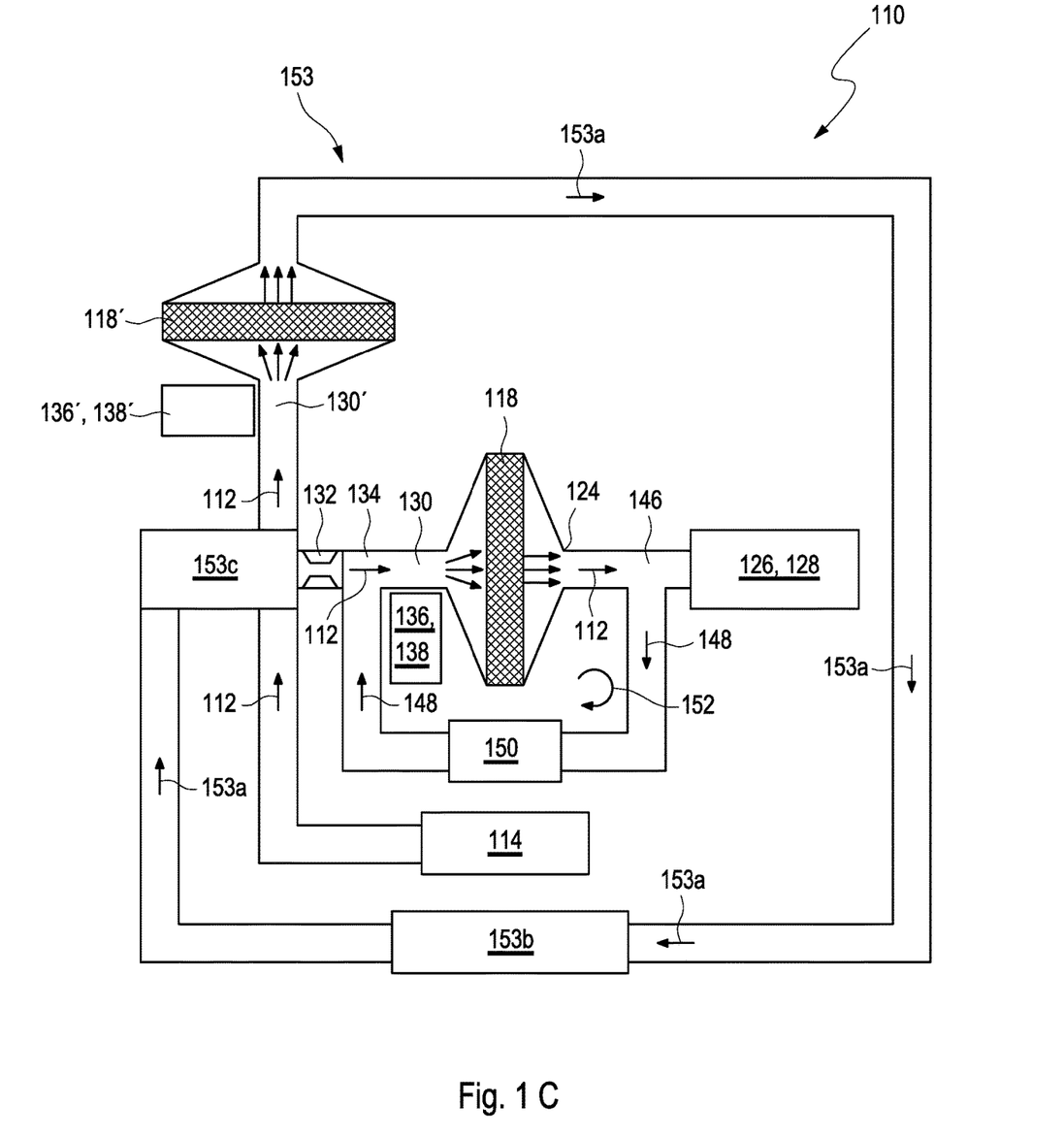

FIG. 1C illustrates a further preferred embodiment of the device 110 which comprises two individual measurement volumes 130, 130'. Herein, the first optical measurement unit 136 is, in a manner similar to the embodiment as illustrated in FIG. 1B, designed for generating at least one first optical measurement signal depending on the interaction of at least one first light beam with the aerosol particles 120 which pass the first measurement volume 130 during an inhalation phase, wherein the evaluation unit (not depicted here) is designed for determining a first aerosol delivery of the aerosol stream 112 during the inhalation phase from the first optical measurement signal. Herein, the patient interface 132 may be used for a simulation of the inhalation phase by sucking particles from the patient interface 132 to the filter 118.

In order to further provide a simulation of an exhalation phase, an exhaled aerosol is guided into a separate exhalation conduct 153 which comprises at least one second optical measurement unit 136' being further designed for generating at least one second optical measurement signal depending on the interaction of at least one second light beam with the aerosol particles 120 passing the second measurement volume 130' during the exhalation phase, wherein the evaluation unit (not depicted here) is designed for determining a second aerosol delivery of the aerosol stream during the exhalation phase from the second optical measurement signal. Hereinafter, the aerosol particles are collected in a second filter 118', whereupon a particle-free gas flow 153a may be generated which can be guided via a device 153b for generating a breathing gas for respiratory support using, e.g., a continuous positive airway pressure (CPAP) or for mechanical ventilation to an adapter 153c to be re-introduced into the aerosol stream 112 which is provided by the aerosol generator 114.

In particular, the embodiment of FIG. 1C can be used for determining the aerosol delivery for preterm infants, specifically together with a device for a respiration-controlled application of aerosol as, for example, disclosed in WO 2018/010954 A1. However, other applications of this embodiment are feasible.

Figure 2:
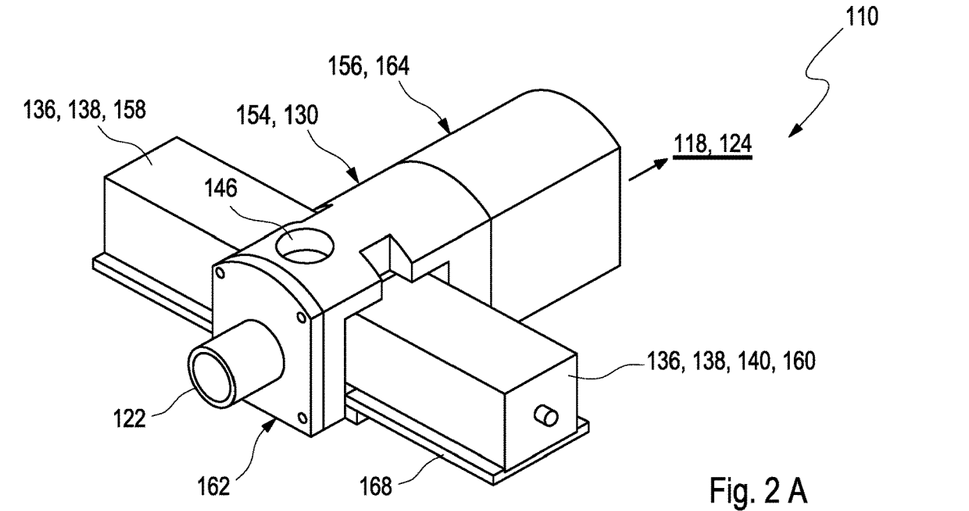
FIGS. 2A to 2C illustrate a preferred embodiment of the device for determining an aerosol delivery of an aerosol stream generated by an aerosol generator in an isometric view (FIG. 2A), a section viewed from the top (FIG. 2B) and a section viewed from the side (FIG. 2C)

FIGS. 2A to 2C illustrate a preferred embodiment of the device 110, however, depicted without the filter 118 and the second fluid connection point 124, for determining the aerosol delivery of the aerosol stream 112 generated by the aerosol generator 114 in an isometric view (FIG. 2A), a section viewed from the top (FIG. 2B) and a section viewed from the side (FIG. 2C). In this preferred embodiment, the device 110 is provided in form of a first partial device 154, a second partial device 156 to which the filter 118 and the second fluid connection point 124 are attached to, a laser emitter 158, and a laser receiver 160. Herein, the first partial device 154 comprises the measurement volume 130 (not visible here), a connection (not depicted here) between the first partial device 154 and a first connector 162 which includes the first fluid connection point 122, and the third fluid connection point 146, whereas the second partial device 156 is a second connector 164 to the filter 118 and the second fluid connection point 124. Further, the optical measurement unit 136 is provided here in form of the laser measurement system 138, wherein, as depicted here, the laser measurement system 138 is divided into the laser emitter 158 and the laser receiver 160. While the laser emitter 158 is designed to provide a laser beam 166, the laser receiver 160 is designated to receive the laser beam 166 and to generate the at least one optical measurement signal depending on the interaction of the laser beam 166 with the aerosol particles 120 passing the measurement volume 130. As further indicated, the evaluation unit 140 which is designed for determining the aerosol delivery of the aerosol stream 112 from the at least one optical measurement signal, is integrated here into the laser receiver 160. However, other embodiments of the evaluation unit 140, such as described above, may also be feasible here. Further, the laser measurement system 138 is placed on a laser mount 168, a preferred embodiment of which is described below in more detail.

Figure 3:
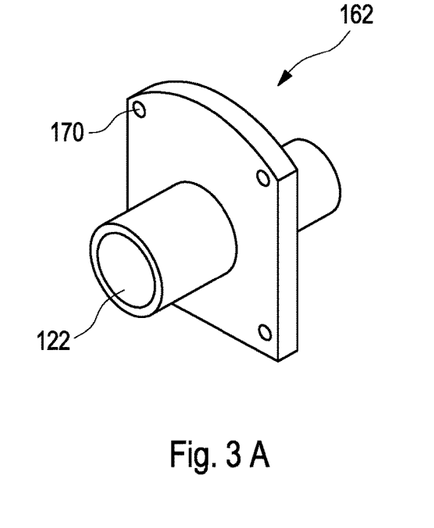
FIGS. 3A and 3B illustrate a preferred embodiment of a first connector in an isometric view (FIG. 3A) and a section viewed from the side (FIG. 3B)

FIGS. 3A and 3B illustrate a preferred embodiment of the first connector 162 in an isometric view (FIG. 3A) and a section viewed from the side (FIG. 3B). As already indicated above, the first connector 162 includes the first fluid connection point 122. As further depicted here, the first connector 162 comprises a connection 170 between the first partial device 154 and the first fluid connection point 122, wherein a distance 172 denotes a length by which the first connector 162 can be introduced into the first partial device 154.

Figure 4:
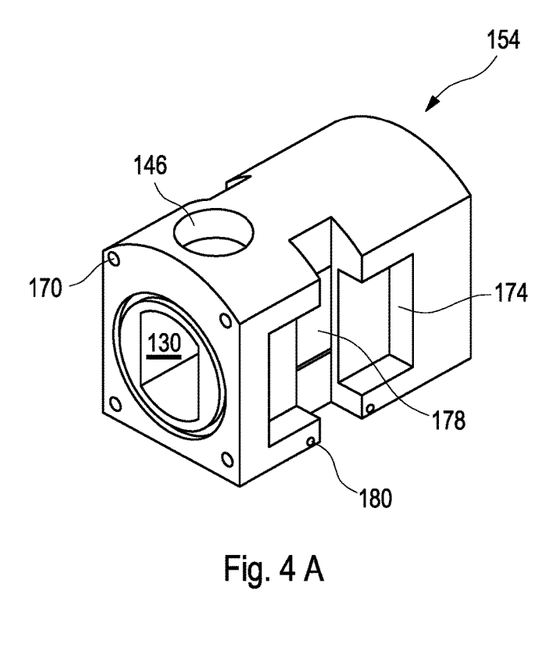
FIGS. 4A and 4B illustrate a preferred embodiment of a first partial device in an isometric view (FIG. 4A) and a back view (FIG. 4B)

FIGS. 4A and 4B illustrate a preferred embodiment of the first partial device 154 in an isometric view (FIG. 4A) and a back view (FIG. 4B). As already indicated above, the first partial device 154 comprises the measurement volume 130, the connection 170 between the first partial device 154 and the first connector 162, and the third fluid connection point 146. As further depicted here, the first partial device 154 may, additionally, comprise at least one first recess 174 for receiving a part of the laser measurement system 138, an optical window 178 which is designated for separating the laser measurement system 138 from the measurement volume 130, and a further connection 180 for receiving the laser mount 168.

In general, the optical windows 178 is designed in a manner that the aerosol stream 112 can be guided through the measurement volume 130 with as little deviation as possible when the light beam enters or leaves the measurement volume 130. Further, the optical windows 178 is designed in a manner that the light beam which, concurrently, passes in through the measurement volume 130 is distracted as little as possible. For this purpose, the optical window 178 may comprise an optically at least partially transparent material, preferably a material which may exhibit a high optical transparency at the at least one wavelength of the light beam. Hereby, the optically at least partially transparent material may, be substantially homogeneous and free of embedded particles. Further, the optical window 178 may, preferably, be arranged in a fashion that the light beam can pass the optical window in a perpendicular manner. Further, the optical window 178 may exhibit a thickness which may be as low a possible, thereby keeping a mechanical stability of the optical window within a desired range.

Further, as illustrated in the particularly preferred embodiment of FIGS. 4A and 4B, the measurement volume 130 may be separated from the optical measurement unit 136 by two opposing optical windows 178 which may be arranged with respect to each other in a parallel manner. Alternatively, tow optical windows 178 can comprise a tilted arrangement with respect to each other.

Further, it may be advantageous to arrange the two opposing optical windows 178 as close as reasonable with respect to each other. Further, it may be advantageous to arrange an illumination source and/or an optical sensor of the optical measurement unit 136 as close as possible to the corresponding optical window 178. Further, a heating unit, such as a heating cabinet (not depicted here), that may be designed for heating one or both of the optical windows 178 can be provided, thus, keeping at least one optical window 178 free from any particle deposition, specifically, thus avoiding an undesired signal loss of a light beam passing an optical window 178 being stained by particle and moisture deposition. However, heating the collecting unit 116 in total or other components thereof may also be feasible.

Figure 5:
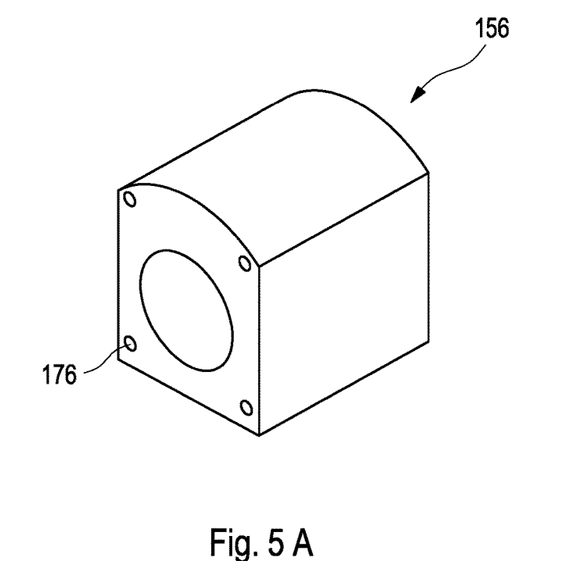
FIGS. 5A and 5B illustrate a preferred embodiment of a second partial device in an isometric view (FIG. 5A) and a section viewed from the top (FIG. 5B)

FIGS. 5A and 5B illustrate a preferred embodiment of the second partial device 156 in an isometric view (FIG. 5A) and a section viewed from the top (FIG. 5B). As already indicated above, the second partial device 156 is designed for providing a connection between the first partial device 154 and the filter 118. For this purpose, the second partial device 156 is, preferably, embodied as the second connector 164 to the filter 118 and, subsequently, the second fluid connection point 124. As further depicted here, the second partial device 156 may, thus, comprise the further connection 176 to the first partial device 154.

Figure 6:
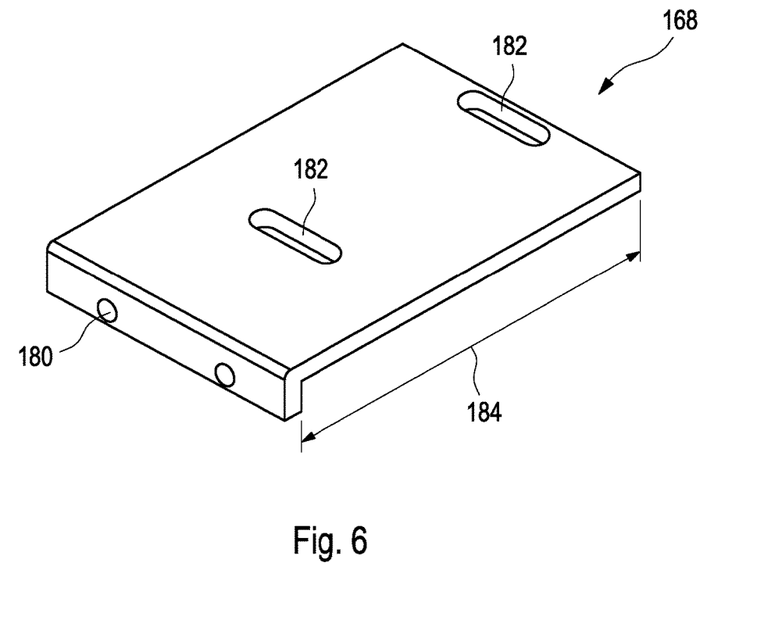
FIG. 6 illustrates a preferred embodiment of a laser mount in an isometric view.

FIG. 6 illustrates a preferred embodiment of the laser mount 168 in an isometric view. As depicted there, the laser mount 168 may, preferably, comprise a further connection 180 to the first partial device 154 and elongated slots 182 which may be designed for providing an adjustable connection to the laser measurement system 138. A distance 184 denotes a length of the laser mount 168 which may, preferably, be selected in a fashion to provide sufficient mechanical stability to the laser measurement system 138.

Figure 7:
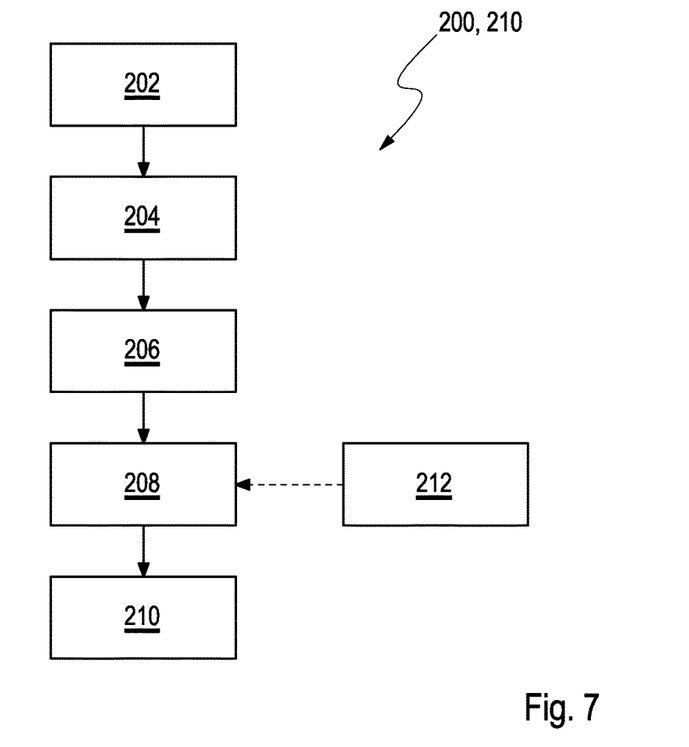
FIG. 7 schematically illustrates the method for determining an aerosol delivery of an aerosol stream.

FIG. 7 schematically illustrates a preferred embodiment of a method 200 for determining an aerosol delivery of an aerosol stream 112 generated by an aerosol generator 114. Accordingly, the aerosol stream 112 as generated by the aerosol generator 114 is provided during step a) as a delivery step 202. During step b), the aerosol particles 120 which are carried by the aerosol stream 122 are guided through the measurement volume 130, whereby, in an interaction step 204, an interaction of the aerosol particles 120 with the at least one light beam within the measurement volume 130 is provided. As a result of this interaction, optical measurement signals which depend on the interaction of the at least one light beam with the aerosol particles 120 which are passing the measurement volume 130 are generated during step c) in a measurement step 206. In a determination step 208, the desired aerosol delivery 210 of the aerosol stream 112 is determined during step d) from the recorded optical measurement signals.

For this purpose, a conversion function, in particular a conversion factor, between the optical measurement signals and the aerosol delivery may be used hereby. Herein, the conversion function, such as the conversion factor, can be taken from a table, such as a table stored in a storage device comprised by the evaluation unit 140. In a particularly preferred embodiment, the conversion function can be determined by performing a calibration step 212 during step e), preferably prior to the determination step 208 but also concurrently with or after the determination step 208, at least a single time, preferably a single time. According to step e), the aerosol particles 120 carried by the aerosol stream 112 are collected in the filter 118, a particle load arising therefrom on the filer 118 is measured, in particular, by a gravimetric determination of the measured load on the filter 118, and the conversion is determined from a relationship between the particle load on the filter 118 and the at least one optical measurement signal.

In a particularly preferred example for this measurement, the filter 118 is weighed and, when inserted into the device 110, loaded with the aerosol particles 120 from a start at a first point of time until an end at a second point of time. As a result, a difference between a second weight measured at the second point of time and a first weight measured at the first point of time allows determining the gravimetric load of the aerosol particles 120 received by the filter 118 between the first point of time and the second point of time. Concurrently, from the optical measurement signals which are recorded for the time interval between the first point of time and the second point of time, an integral over the optical measurement signals of the aerosol particles 120 between the first point of time and the second point of time can be determined. By generating a relationship between the integral of the optical measurement signals and the gravimetrically determined load of the same aerosol particles 120 within the same aerosol stream 112, the conversion function, such as the conversion factor, can be determined. This procedure according to step e) can, if desired, be repeated several times, preferably for different particle loads, such as to determine the conversion function with a desired accuracy.

Figure 8:
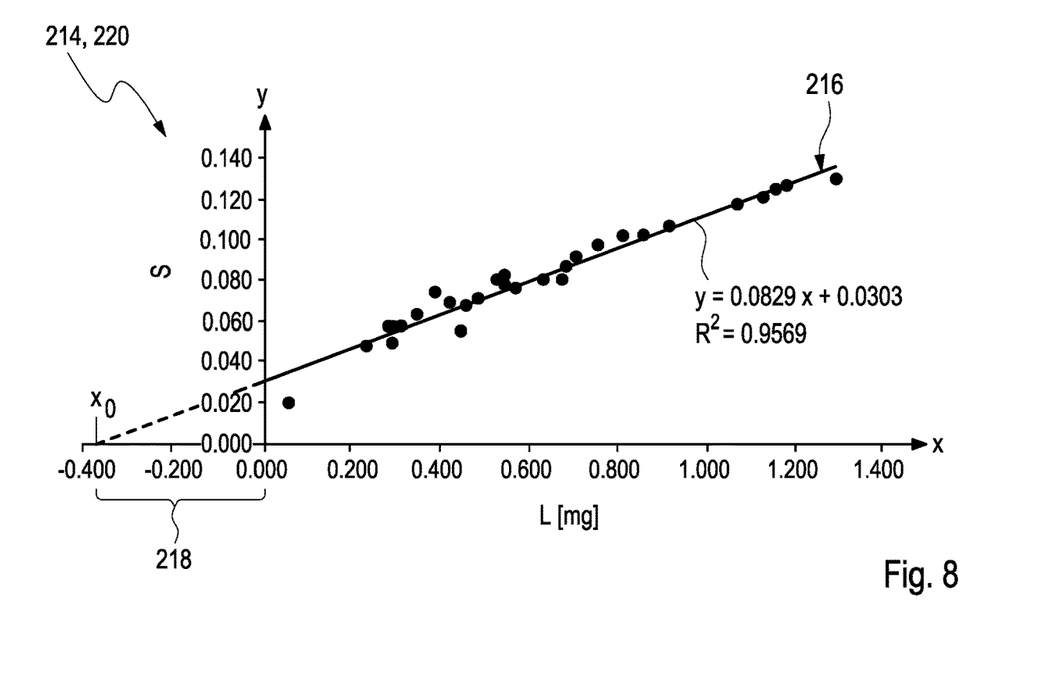
FIG. 8 illustrates a relationship between an optical signal and a gravimetric load of the aerosol particles.

A preferred example for the relationship between the optical signal and the gravimetric load of the same aerosol particles 120 is shown in FIG. 8. In a diagram 214, various optical signals S relating to light extinction, such as by $$S=\log(I_0/I),$$

wherein $I_0$ indicates an intensity of the light beam prior to passing through the measurement volume 130, I an intensity of the light beam after passing through the measurement volume, and log indicates a logarithm to any known basis, are presented on a vertical y-axis over the gravimetric load L [mg] of the same aerosol particles 120 which are presented as a measured point over a horizontal x-axis of this diagram 214. In particular by applying a linear fitting procedure, such as a linear regression, a resulting line 216 may be obtained as the relationship between the optical signal and the gravimetric load of the same aerosol particles 120. By way of example, the relationship may be described by the Equation:

$$y=0.0829x+0.0303,$$

wherein y relates to the extinction calculated from an amplitude of the optical signals S at the corresponding gravimetric load L at the location x on the x-axis. Alternatively or in addition, other procedures, such as other regression algorithms, may be applied here for the determining of this relationship. Alternatively or in addition, other kinds of alterations of the light beam may be measured by the optical measurement unit 136, such an alteration of a diffraction, a reflection, a refraction, a scattering, or a polarization of the light beam.

Subsequently, further considering a known value for the aerosol stream 112, the conversion function, such as the conversion factor, which may be determined in this fashion can be used during the determination step 208 without being required to repeat the calibration step 212. As indicated above, preferably a single gravimetric determination of the load of the aerosol particles 120 is sufficient for determining an aerosol delivery 210 of the aerosol stream 112. It is, nevertheless, still possible to repeat the calibration step 212, if desired.

Alternatively or in addition to being used for the calibration step 212, the diagram 214 as of FIG. 8 can also be applied in a method for determining an absorption and/or adsorption of a liquid 220 on the aerosol particles 120. As schematically illustrated in FIG. 8, the optical measurement signal is measured during step f) for at least two different loads of the aerosol particles 120 on the filter 118, wherein the each of the loads of the aerosol particles 120 on the filter 118 is also determined in a gravimetric fashion as described above. From the various optical measurement signals as shown in FIG. 8, an extrapolated particle load $x_0$ for a zero optical measurement signal can be determined by employing the same regression algorithm, such as the linear regression, as described above. In the example as described above, a value of $x_0=-0.36$ can be obtained for y=0. The intersection of the linear regression with the negative x-axis can, thus, provide a value 218 which corresponds to the mass of the absorbed and/or adsorbed liquid on the aerosol particles 120, thus, allowing the determination of the mass and/or weight of the absorption and/or adsorption of the liquid on the aerosol particles 120.

LIST OF REFERENCE NUMBERS 110 device
112 aerosol stream
114 aerosol generator
116 collecting unit
118, 118' filter
120 aerosol particles
122 first fluid connection point
124 second fluid connection point
126 breathing simulator
128 sinusoidal pump
130, 130' measurement volume
132 area for patient interface
134 conduct
136, 136' optical measurement unit
138, 138' laser measurement system
140 evaluation unit
142 lead
144 monitor
146 third fluid connection point
148 gas stream
150 centrifugal pump
152 closed circuit
153 exhalation conduct
153a particle-free gas flow 153b device for generating a breathing gas for respiratory support using a continuous positive airway pressure (CPAP) or for mechanical ventilation
153c adapter
154 first partial device
156 second partial device
158 laser emitter
160 laser receiver
162 first connector
164 second connector
166 laser beam
168 laser mount
170 connection
172 distance
174 recess
176 further connection
178 optical window
180 further connection
182 elongated slot
184 Distance
200 method for determining an aerosol delivery
202 delivery step
204 interaction step
206 measurement step
208 determination step
210 aerosol delivery
212 calibration step
214 diagram
216 line
218 measurement signal for the extrapolated zero particle load
220 method for determining an absorption and/or adsorption of a liquid

What is claimed is:

1. A device for determining an aerosol delivery of an aerosol stream generated by an aerosol generator, the device comprising:
   a collector, the collector comprising:
   a filter designated for collecting aerosol particles carried by an aerosol stream,
   a first fluid connection point which is connectable to an aerosol generator, and
   a second fluid connection point which is connectable to a breathing simulator being designated for simulating tidal breathing;
   at least one measurement volume, which is designed for an interaction of at least one light beam with the aerosol particles carried by the aerosol stream and passing through the measurement volume;
   at least one optical measurement unit, which is designed for generating at least one optical measurement signal depending on the interaction of the at least one light beam with the aerosol particles passing the measurement volume;
   at least one evaluation unit, which is designed for determining the aerosol delivery of the aerosol stream from the at least one optical measurement signal; and
   two individual measurement volumes,
   wherein at least second one optical measurement unit is further designed for generating at least one second optical measurement signal depending on the interaction of at least one second light beam with the aerosol particles passing a second measurement volume in an exhalation phase.

2. The device of claim 1, wherein the optical measurement unit is designed for generating the optical measurement signal depending on at least one of an extinction or a scattering of the light beam in the measurement volume upon the passing of the aerosol particles.

3. The device of claim 1, wherein the optical measurement unit is or comprises a laser measurement system, wherein the laser measurement unit is further designed for providing the at least one light beam.

4. The device of claim 1, wherein the light beam is adapted to illuminate a sheet within the measurement volume.

5. The device of claim 1, wherein the measurement volume is separated from the optical measurement unit by at least one optical window, wherein the optical window is designated for being passed by the at least one light beam when entering or leaving the measurement volume, wherein the optical window comprises an optically at least partially transparent material.

6. The device of claim 5, wherein the optically at least partially transparent material is homogeneous and free of embedded particles.

7. The device of claim 5, wherein the optical window is arranged in a fashion that the light beam passes the optical window in a perpendicular manner.

8. The device of claim 5, further comprising a heater being designated for heating the at least one optical window.

9. The device of claim 1, wherein the measurement volume comprises an internal surface which is smooth and free of edges, recesses and protrusions.

10. The device of claim 1, wherein the first fluid connection point is located, with respect to a direction of the aerosol stream, in front of the filter.

11. The device of claim 10, wherein the measurement volume is located between the first fluid connection point and the filter.

12. The device of claim 1, wherein the collector has at least one third fluid connection point which is connected with a gas flow unit for generating a gas stream, wherein the third fluid connection point is arranged in a manner that the aerosol stream is at least partially directed by the gas stream to the filter.

13. The device of claim 1, wherein at least one first optical measurement unit is designed for generating at least one first optical measurement signal depending on the interaction of at least one first light beam with the aerosol particles passing a first measurement volume in an inhalation phase.

14. The device of claim 13, wherein the evaluation unit is designed for determining a first aerosol delivery of the aerosol stream during the inhalation phase from the first optical measurement signal.

15. The device of claim 1, wherein the evaluation unit is designed for determining a second aerosol delivery of the aerosol stream during the exhalation phase from the second optical measurement signal.

16. A method for determining an aerosol delivery of an aerosol stream, the method comprising the following steps:
   a) providing an aerosol stream generated by an aerosol generator;
   b) guiding aerosol particles carried by the aerosol stream through at least one measurement volume and providing an interaction of the aerosol particles with at least one light beam within the measurement volume;
   c) generating at least one optical measurement signal depending on the interaction of the at least one light beam with the aerosol particles passing the measurement volume; and
   d) determining the aerosol delivery of the aerosol stream from the at least one optical measurement signal, wherein a conversion function between the optical measurement signal and the aerosol delivery is used, wherein the conversion function is determined by performing the following step e) at least one single time:

e) collecting the aerosol particles carried by the aerosol stream in a filter, measuring a particle load on the filer; and determining the conversion function from a relationship between the particle load and the at least one optical measurement signal, and wherein the method comprising steps a) to e) and the following step f):

f) generating at least two optical measurement signals for at least two different particle loads of the aerosol particles, measuring the at least two different particle loads of the aerosol particles on at least two different filters, and determining at least one of the absorption or the adsorption of the liquid on the aerosol particles from an assumed zero optical measurement signal.

* * * * *